(12) United States Patent
Schwartzer et al.

(10) Patent No.: US 12,188,916 B2
(45) Date of Patent: Jan. 7, 2025

(54) MEANS AND METHODS FOR SCORING VEGETABLES AND FRUITS

(71) Applicant: CLARIFRUIT LTD., Rishon LeZion (IL)

(72) Inventors: Avi Schwartzer, Irus (IL); Ruby Boyarski, Ness Ziona (IL)

(73) Assignee: CLARIFRUIT LTD., Rishon LeZion (IL)

( * ) Notice: Subject to any disclaimer, the term of this patent is extended or adjusted under 35 U.S.C. 154(b) by 357 days.

(21) Appl. No.: 17/597,620

(22) PCT Filed: Jul. 13, 2020

(86) PCT No.: PCT/IL2020/050785
§ 371 (c)(1),
(2) Date: Jan. 14, 2022

(87) PCT Pub. No.: WO2021/009753
PCT Pub. Date: Jan. 21, 2021

(65) Prior Publication Data
US 2022/0252568 A1     Aug. 11, 2022

Related U.S. Application Data

(60) Provisional application No. 62/874,131, filed on Jul. 15, 2019.

(51) Int. Cl.
*G01N 33/02* (2006.01)
*G01N 21/359* (2014.01)
(Continued)

(52) U.S. Cl.
CPC ......... *G01N 33/025* (2013.01); *G01N 21/359* (2013.01); *G01N 21/95* (2013.01); *G06Q 50/02* (2013.01); *G01N 2021/8466* (2013.01)

(58) Field of Classification Search
CPC .... G01N 33/025; G01N 21/359; G01N 21/95; G01N 2021/8466; G01N 21/31; G01N 21/4133; G06Q 50/02
See application file for complete search history.

(56) References Cited

U.S. PATENT DOCUMENTS

| | | | | |
|---|---|---|---|---|
| 2002/0011567 A1* | 1/2002 | Ozanich | ................ | G01J 3/0224 250/326 |
| 2006/0118726 A1* | 6/2006 | Kawabata | .......... | G01N 21/3563 250/358.1 |

(Continued)

OTHER PUBLICATIONS

Barrett et al., "Color, Flavor, Texture, and Nutritional Quality of Fresh-Cut Fruits and Vegetables: Desirable Levels, Instrumental and Sensory Measurement, and the Effects of Processing", Critical Reviews in Food Science and Nutrition, 2010, vol. 50, pp. 369-389.

(Continued)

*Primary Examiner* — Lisa M Caputo
*Assistant Examiner* — Cynthia L Davis
(74) *Attorney, Agent, or Firm* — Vorys, Sater, Seymour and Pease LLP; Anthony P. Venturino; Maryellen Feehery Hank

(57) ABSTRACT

Configurable application, for scoring an object including: configuration interface to: receive configuration parameters for each object including: a. a list of attributes to be associated with an object; b. a maximum total score; c. for each attribute in the attributes list: minimum value, maximum value, and weight; and d. configuration type; and a processing unit to calculate scoring for the object according to the received configuration parameters, by: receiving a value for each attribute in the object's attributes list; comparing each attribute value against a predefined minimum and maximum; calculating total score according to a predefined formula, when the attribute value is within the range of the minimum and maximum; calculating total score based (Continued)

on configuration type, when the attribute value is outside the minimum and maximum range; displaying the total score to a user via a display unit. The calculating is performed only when all attributes have values.

9 Claims, 5 Drawing Sheets

(51) Int. Cl.
*G01N 21/84* (2006.01)
*G01N 21/95* (2006.01)
*G06Q 50/02* (2024.01)

(56) References Cited

U.S. PATENT DOCUMENTS

| | | | | |
|---|---|---|---|---|
| 2014/0137877 A1* | 5/2014 | Deevi | ............... | G01N 21/84 356/303 |
| 2018/0042178 A1* | 2/2018 | Nakano | ............ | G01N 21/359 |
| 2018/0209901 A1 | 7/2018 | Schwartzer et al. | | |
| 2018/0252691 A1* | 9/2018 | Blanc | ............... | G01N 33/025 |
| 2018/0259496 A1* | 9/2018 | McPeek | ............ | G01N 33/025 |
| 2018/0365820 A1 | 12/2018 | Nipe et al. | | |
| 2022/0137019 A1* | 5/2022 | Dasari | ............. | G06Q 10/06395 702/19 |
| 2022/0307905 A1* | 9/2022 | De Geus | ............ | G01J 3/0202 |

OTHER PUBLICATIONS

Pu et al., "Recent Progress of Hyperspectral Imaging on Quality and Safety Inspection of Fruits and Vegetables: A Review", Comprehensive Reviews in Food Science and Food Safety, 2015, vol. 14, pp. 176-188.

Ennis et al., "Hyperspectral database of fruits and vegetables", Journal of the Optical Society of America A, 2018, 12 pages.

Extended European Search Report filed in corresponding EP application No. 20840974.8, dated Jun. 27, 2022, 9 Pages.

* cited by examiner

MEANS AND METHODS FOR SCORING VEGETABLES AND FRUITS

FIELD OF THE INVENTION

The present invention relates generally to evaluating substance. More specifically, the present invention relates to using a computing device, sensors and algorithms to determine attributes and characteristics of a vegetables or fruits.

BACKGROUND OF THE INVENTION

The need to evaluate fruits and vegetables is known in the art. For example, the ripeness of a fruit is of crucial importance to a buyer and/or grower of the fruit, the sugar level is of crucial importance when using vegetables to feed livestock and so on. Factors affecting fruits and vegetables can be quantified visually which is laborious, expensive and is easily affected by physical factors, including inconsistent evaluation and subjective results. For example, by merely looking at a fruit (e.g., a watermelon or avocado), it may be impossible to determine ripeness, sugar level and the like or determine how long the fruit has been shelved.

Thus, there is a need for readily and quickly, using a small, portable computing device evaluating attributes of a fruits or vegetables in a remote manner. Furthermore, there is a need for automatically rating score calculation of fruits and vegetables.

SUMMARY OF THE INVENTION

There is thus provided, in accordance with some embodiments of the present disclosure a configurable application for scoring an object. The configurable application may include: a configuration interface. The configuration interface may be arranged to: receive configuration parameters for each object from a user, wherein the configuration parameters include: (a) a list of attributes to be associated with an object; (b) a maximum total score; (c) for each attribute in the list of attributes: (i) a minimum value; (ii) a maximum value; and (iii) weight, and (d) a type of configuration; and also a processing unit. The processing unit may be arranged to calculate scoring for the object according to the received configuration parameters, by: (a) receiving a value for each attribute in the attributes list that is associated with the object; (b) comparing each attribute value against a predefined minimum value and a predefined maximum value; (c) calculating a total score according to a predefined formula, when the attribute value is in the range of the predefined minimum value and the predefined maximum value; (d) calculating the total score based on the type of configuration, when the attribute value is not in the range of the predefined minimum value and the predefined maximum value; and (e) displaying the total score to the user via a display unit.

In accordance with some embodiments of the present disclosure, the calculating is performed only when all attributes have values Furthermore, in accordance with some embodiments of the present disclosure, the object may be a vegetable or a fruit.

Furthermore, in accordance with some embodiments of the present disclosure, the type of configuration may be selected out of: (i) "high"; (ii) "low"; or (iii) "middle".

Furthermore, in accordance with some embodiments of the present disclosure, the processing unit may be further arranged to score each attribute by: when the type of configuration is "high":
  i. when the attribute value is less than the predefined minimum value, scoring the attribute score as zero;
  ii. when the attribute value is more than the predefined maximum value, scoring the attribute value as the predefined maximum value;
when the type of configuration is "middle":
  i. when the attribute value is less than the predefined minimum value, scoring the attribute score as zero;
  ii. when the attribute value is more than the predefined maximum value, scoring the attribute value zero;
when the type of configuration is "low":
  i. when the attribute value is less than the predefined minimum value, scoring the attribute value as the predefined maximum value;
  ii. when the attribute value is more than the predefined maximum value, scoring the attribute value as zero.

Furthermore, in accordance with some embodiments of the present disclosure, the predefined minimum value and the predefined maximum value may be retrieved from a database of statistics values of the object.

Furthermore, in accordance with some embodiments of the present disclosure, the predefined formula may be: (the attribute value–the predefined minimum value)/(the predefined maximum value–the predefined minimum value) *the weight.

Furthermore, in accordance with some embodiments of the present disclosure, the processing unit may be further arranged to receive from the user a number of multiple-level scoring groups.

Furthermore, in accordance with some embodiments of the present disclosure, the processing unit may be further arranged to associate the total score with a scoring group in the number of multiple-level scoring groups and display it to the user via a display unit.

Furthermore, in accordance with some embodiments of the present disclosure, each attribute in the list of attributes may have a termination flag associated to it, wherein the user configures as turned off or turned on. When the termination flag of an attribute is turned on, the processing unit is further arranged to zero the total score based on the configuration type.

Furthermore, in accordance with some embodiments of the present disclosure, when the configuration type is "high" the processing unit is further arranged to check if the attribute value is less than the predefined minimum; when the configuration type is "middle" the processing unit is further arranged to check if the attribute value is less than the predefined minimum and more than the predefined maximum; and when the configuration type is "low" the processing unit is further arranged to check if the attribute value is more than the predefined maximum.

Furthermore, in accordance with some embodiments of the present disclosure, the configurable application is cloud based.

Furthermore, in accordance with some embodiments of the present disclosure, the received value for each attribute in the attributes list is based on image analysis results and on reflection analysis results of the object.

Furthermore, in accordance with some embodiments of the present disclosure, when a user configures a minimum value which is higher than the value which has been retrieved from the database of statistics, the calculating of a score of the attribute is performed according to association to predefined groups.

Furthermore, in accordance with some embodiments of the present disclosure, said attribute is selected from the group consisting of BRIX (%), Firmness (sh), Size (mm), Dry Weight (%), Quality Defect, Condition Defect, Color range, Stem Color, Acidity, Hue, Color Variance, Appearance, Color Coverage (%), Starch (%), Size Group, Color Coverage Group, Weight, Juice (%), Seeds (%), Temperature, TSS/Acidity and any combination thereof.

Furthermore, in accordance with some embodiments of the present disclosure, said defect is selected from the group consisting of color defect, skin defect, healed wounds, insect damage, cracks, softness, decay, handling damage, dehydration, pests, over mature, disease damage, freezing damage, bruising hail damage or any other extreme weather condition damage, bird damage, bitter pit, bleeding, brown berries, burnt berries, cork, cracks, creasing, foreign bodies, humidity damage, internal breakdown, mold, oleocellosis, split seed, open stones, wounds, pedicle tear, pitting, puffed scald, scars, shatter shelling, soft shoulder, split berries, thin peel, unhealed wounds, watercore, watery, weak, berry drop, black navel, bottleneck, broken berries, Clusters or Triples, defect in shape, deformed. dirty/dusty, green fruits, immature fruits, inking, lenticel, long peduncle, mealybug, moth, navel tear, no pedicle, Oidium, open navel, pendulum, pests, poorly brushed, powdery mildew, presence of pedicel, protruding navel, Pruina, rest of flower, Round Rugged Russet, scurfy silver, soft scale, sooty mold, split, stains, sunburn, tight, underweight, undersized, waste, without Rosetta, and any other fruit or vegetable defect and any combination thereof.

Furthermore, in accordance with some embodiments of the present disclosure, the processing unit uses a machine learning algorithm.

Furthermore, in accordance with some embodiments of the present disclosure, the machine learning algorithm uses verified training data.

It is a further object of the present invention to disclose a method of non-destructively determining characteristics of a vegetable or fruit, the method comprising:
creating at least one profile for a cultivar of a vegetable or fruit;
processing an image of a vegetable or fruit to produce image analysis results;
analyzing hyperspectral and/or Near Infrared (NIR) illumination reflected from the vegetable or fruit to produce reflection analysis results; and
calculating, and presenting to a user, a score for the vegetable or fruit based on matching the image and reflection analyses results with the profile using the configurable application as defined in any of the above.

It is a further object of the present invention to disclose the method as defined above, wherein the profile and the analysis results include a value that represents a ripeness and a value that represents a quality.

It is a further object of the present invention to disclose the method as defined in any of the above, further comprises steps of analyzing a value using a device selected from the group consisting of: a refractometer, a pH meter, acidometer, penetrometer, durometer, temperature meter and any combination thereof.

It is a further object of the present invention to disclose the method as defined in any of the above, wherein said analyzing step comprises analyzing a value selected from the group consisting of: BRIX %, firmness, size, dry weight %, quality defect, condition defect, color range, stem color, acidity, hue, color variance, appearance, color coverage, starch (%), size group (%), color coverage group, weight, juice (%), seeds (%), temperature, TSS/acidity and any combination thereof.

It is a further object of the present invention to disclose the method as defined in any of the above, wherein said analyzing step comprises analyzing a defect type selected from the group consisting of color defect, skin defect, healed wounds, insect damage, cracks, softness, decay, handling damage, dehydration, pests, over mature, disease damage, freezing damage, bruising hail damage or any other extreme weather condition damage, bird damage, bitter pit, bleeding, brown berries, burnt berries, cork, cracks, creasing, foreign bodies, humidity damage, internal breakdown, mold, oleocellosis, split seed, open stones, wounds, pedicle tear, pitting, puffed scald, scars, shatter shelling, soft shoulder, split berries, thin peel, unhealed wounds, watercore, watery, weak, berry drop, black navel, bottleneck, broken berries, Clusters or Triples, defect in shape, deformed, dirty/dusty, green fruits, immature fruits, inking, lenticel, long peduncle, loose low color, mealybug, moth, navel tear, no pedicle, Oidium, open navel, pendulum, pests, poorly brushed, powdery mildew, presence of pedicel, protruding navel, Pruina, rest of flower, Round Rugged Russet, scurfy silver, soft scale, sooty mold, split, stains, sunburn, tight, underweight, undersized, waste, without Rosetta, and any other fruit or vegetable defect and any combination thereof.

It is a further object of the present invention to disclose the method as defined in any of the above, further comprising:
obtaining a cultivar of the vegetable or fruit; and
calculating the at least one value based on the cultivar.

It is a further object of the present invention to disclose the method as defined in any of the above, further comprising calculating the score based on at least one of: a geographic region and a date.

It is a further object of the present invention to disclose the method as defined in any of the above, further comprising:
receiving an image of a plurality of vegetables or fruits; and
calculating, for the plurality of vegetables or fruit, scores of the best and worst vegetable or fruit.

It is a further object of the present invention to disclose the method as defined in any of the above, further comprising calculating a prediction related to at least one of: harvesting and treating of crops.

It is a further object of the present invention to disclose the method as defined in any of the above, further comprising:
receiving, from a plurality of users, profiles and associated scores; and
creating the profile and associating the profile with a score based on the profiles and associated scores received from the users.

It is a further object of the present invention to disclose the method as defined in any of the above, further comprising using input from a plurality of users for at least one of: creating the profile and calculating the score.

It is a further object of the present invention to disclose the method as defined in any of the above, further comprising:
designating at least one of: a profile and a score, as a reference; and
calculating the at least one value based on comparing at least one reference to at least one of: the image analysis results and the reflection analysis results.

It is a further object of the present invention to disclose the method as defined in any of the above, further comprising: causing a machine to select a fruit or vegetable based on at least one of: a profile and a score.

It is a further object of the present invention to disclose a system comprising:
a memory; and
a controller configured to:
create at least one profile for a cultivar of a vegetable or fruit;
process an image of the vegetable or fruit to produce image analysis results;
analyze hyperspectral and/or Near Infrared (NIR) illumination reflected from the vegetable or fruit to produce reflection analysis results; and
calculate, and present to a user, a score for the vegetable or fruit based on matching the image and reflection analyses results with the profile using said configurable application according to the claims.

It is a further object of the present invention to disclose the system as defined above, wherein the profile and the analyses results include a first value that represents a ripeness and a second value that represents a quality.

It is a further object of the present invention to disclose the system as defined in any of the above, wherein said controller is configured to analyze a value obtainable using a device selected from the group consisting of: a refractometer, a pH meter, acidometer, penetrometer, durometer, temperature meter and any combination thereof.

It is a further object of the present invention to disclose the system as defined in any of the above, wherein said controller is configured to analyze a value selected from the group consisting of: BRIX %, firmness, size, dry weight %, quality defect, condition defect, color range, stem color, acidity, hue, color variance, appearance, color coverage, starch (%), size group (%), color coverage group, weight, juice (%), seeds (%), temperature, TSS/acidity and any combination thereof.

It is a further object of the present invention to disclose the system as defined in any of the above, wherein said controller is configured to analyze a defect type selected from the group consisting of color defect, skin defect, healed wounds, insect damage, cracks, softness, decay, handling damage, dehydration, pests, over mature, disease damage, freezing damage, bruising hail damage or any other extreme weather condition damage, bird damage, bitter pit, bleeding, brown berries, burnt berries, cork, cracks, creasing, foreign bodies, humidity damage, internal breakdown, mold, oleocellosis, split seed, open stones, wounds, pedicle tear, pitting, puffed scald, scars, shatter shelling, soft shoulder, split berries, thin peel, unhealed wounds, watercore, watery, weak, berry drop, black navel, bottleneck, broken berries, Clusters or Triples, defect in shape, deformed, dirty/dusty, green fruits, immature fruits, inking, lenticel, long peduncle, loose low color, mealybug, moth, navel tear, no pedicle, Oidium, open navel, pendulum, pests, poorly brushed, powdery mildew, presence of pedicel, protruding navel, Pruina, rest of flower, Round Rugged Russet, scurfy silver, soft scale, sooty mold, split, stains, sunburn, tight, underweight, undersized, waste, without Rosetta, and any other fruit or vegetable defect and any combination thereof.

It is a further object of the present invention to disclose the system as defined in any of the above, wherein the controller is further configured to at least one of:
a. calculate the at least one value based on at least one of: a geographic region and a date.
b. receive an image of a plurality of vegetables or fruit; and
calculate, for the plurality of vegetables or fruit, scores of the best and worst vegetables or fruits;
c. calculate a prediction related to at least one of: harvesting and treating of crops; and
d. receive, from a plurality of users, profiles and associated scores; and
create the profile and associate the profile with a score based on the profiles and associated scores received from the users.

It is a further object of the present invention to disclose the system as defined in any of the above wherein the controller is further configured to
a. use input from a plurality of users for at least one of: creating the profile and calculating the score;
b. designate at least one of: a profile and a score, as a reference; and
calculate the at least one value based on comparing at least one reference to at least one of: the image analysis results and the reflection analysis results; and
c. cause a machine to select a fruit or vegetable based on at least one of: a profile and a score.

It is a further object of the present invention to disclose a method of non-destructively determining characteristics of a vegetable or fruit, the method comprising:
(a) receiving a training set of hyperspectral data using a system comprising;
(i) a memory; and
(ii) a controller configured to:
create at least one profile for a cultivar of a vegetable or fruit;
process an image of the vegetable or fruit to produce image analysis results;
analyze hyperspectral illumination reflected from the vegetable or fruit to produce reflection analysis results; and
calculate, and present to a user, a score for the vegetable or fruit based on matching the image and reflection analyses results with the profile;
(b) applying a machine learning algorithm to said training set of hyperspectral data to provide predictor parameters for said vegetable or fruit profile;
(c) receiving measurement hyperspectral data from a vegetable or fruit of interest; and using said predictor parameters to score said vegetable or fruit of interest.
wherein said training set of hyperspectral data, and said measurement hyperspectral data comprise reflection spectra across wavelength bands of light that include at least visible, near infrared and short-wave infrared regions of the electromagnetic spectrum.

BRIEF DESCRIPTION OF THE INVENTION

Figure 1:
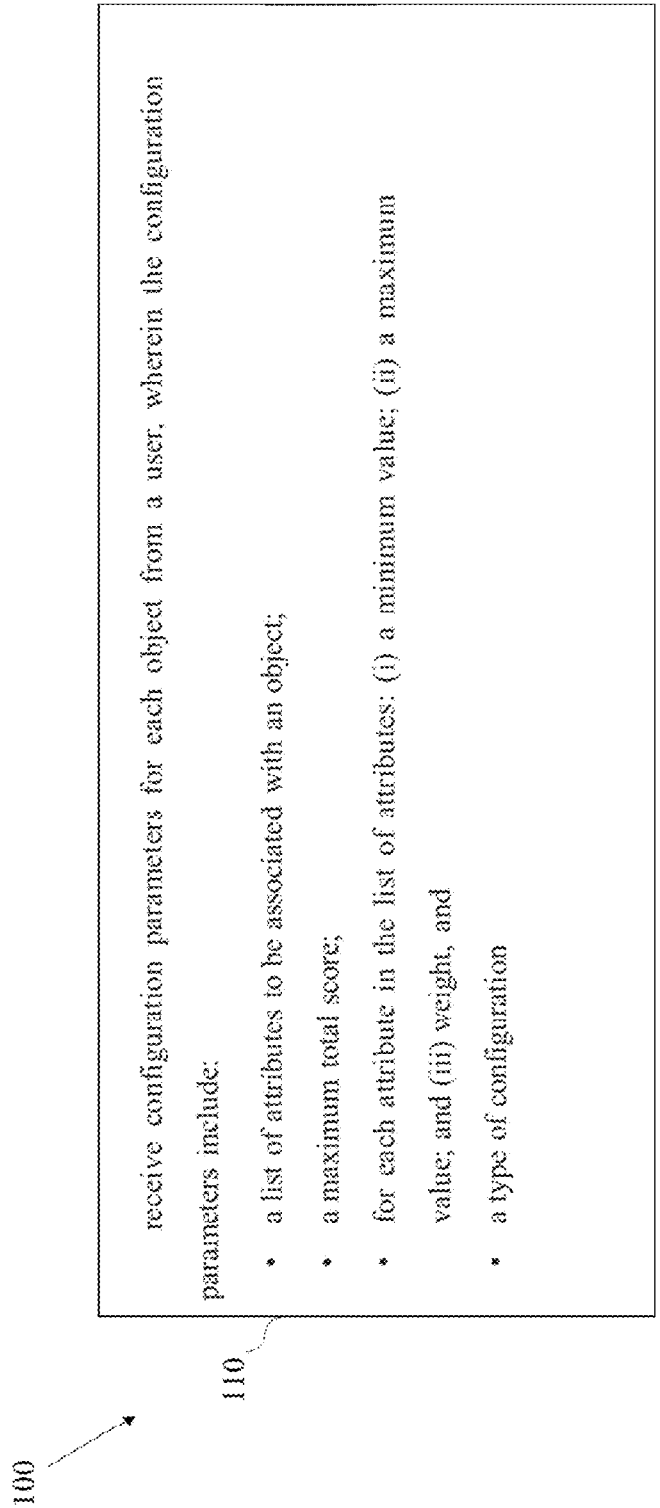
FIG. 1 is a high-level flow diagram depicting a configuration interface to configure an application, in accordance with some embodiments of the present disclosure.

It will be appreciated that, for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the disclosure. However, it will be understood by those of ordinary skill in the art that the disclosure may be practiced without these specific details. In other instances, well-known methods, procedures, components, modules, units and/or circuits have not been described in detail so as not to obscure the disclosure.

Although embodiments of the disclosure are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the disclosure are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, use of the conjunction "or" as used herein is to be understood as inclusive (any or all of the stated options).

Nowadays, when a vendor of an application is implementing the application at a client's site, the configuration of the specific parameters into the application requires a proficient or a licensed technician. There is also an additional level of complexity in applications for scoring an object due to multiple and complicated rules which are related to the scoring procedure. Commonly, to tailor the application to the client's business needs, the vendor designates the client with a technician which is provided with the business specifications of the client. The business specifications include the relevant parameters for the required scoring, which must be inserted directly into the code of the application.

In other words, current vendors do not provide the client with a convenient and simple configurable application to manage the configuration of the parameters which are relevant to the specific business needs thus tying the configuration of the application to a proficient technician instead of configuring it by an ordinary and unskilled user.

Hence, there is a need for a configurable application for scoring an object. There is a need to simplify the configuration of the application for scoring an object such that an ordinary and unskilled user will be able to tailor the application to the specific business needs i.e., score related rules.

The configurable application provided according to the present disclosure, enables to overcome the need for a proficient user to configure an application for scoring an object by providing an interface on top of the source code to configure the multiple rules related to the scoring of the object. Thus, the configurable application provided according to the present disclosure saves business resources such as time and costs for the client.

Therefore, by having a configuration interface and a processing unit that is arranged to perform the scoring, the configurable application solves the problem of inserting parameters related to the scoring directly to the source code by a proficient user only.

As used herein, the term about denotes ±25% of the defined amount or measure or value.

As used herein, the term "configuration interface" refers to a module that enables a user to enter parameters to configure score calculations.

As used herein, the term "hyperspectral" or "hyperspectral imaging" or "HIS" refers herein after to a spectral imaging technique which collects and processes information from across the electromagnetic spectrum. The goal of hyperspectral imaging is to obtain the spectrum for each pixel in the image of a scene, with the purpose of finding objects, identifying materials, or detecting processes. In general there are two branches of spectral imagers. There are push broom scanners and the related whisk broom scanners, which read images over time, and snapshot hyperspectral imaging, which uses a staring array to generate an image in an instant. In other words, hyperspectral imaging, or imaging spectroscopy, combines the power of digital imaging and spectroscopy. For each pixel in an image, a hyperspectral camera acquires the light intensity (radiance) for a large number (typically a few tens to several hundred) of contiguous spectral bands. Every pixel in the image thus contains a continuous spectrum (in radiance or reflectance) and can be used to characterize the objects in the scene with great precision and detail.

It is further within the scope of the present invention that in hyperspectral imaging, the recorded spectra have fine wavelength resolution and cover a wide range of wavelengths. Hyperspectral imaging measures continuous spectral bands.

It is acknowledged that hyperspectral deals with imaging narrow spectral bands over a continuous spectral range, producing the spectra of all pixels in the scene. For example, a sensor with only 20 bands can also be hyperspectral when it covers the range from 500 to 700 nm with 20 bands each 10 nm wide.

NIR hyperspectral imaging (NHI) is another NIR technology for chemical characterization and has been shown to be a useful tool in the characterization of biological materials. The image has spatial coordinates in two dimensions as well as a wavelength coordinate, yielding a three-dimensional hypercube. According to further embodiments, NIR hyperspectral imaging provides NIR spectral data as a set of images, each representing a narrow wavelength range or spectral band. The advantage compared to NIR spectroscopy is that, due to the additional spatial dimension provided by this technology, the images can be analyzed and visualized as chemical images providing identification as well as localization of chemical compounds in non-homogenous samples.

It is further acknowledged that hyperspectral imaging is a chemical imaging technique based on reflectance spectroscopy (the light reflected by materials). Such a device makes the collection of reflectance spectra in each point of the field of view for the Near Infrared range (it may be complementary to another device for the visible range). The hyperspectral image cube obtained can be considered both as a stack of wavelength-resolved images and as a series of spectra.

It is noted that the term "multispectral" generally refers to an image produced by sensors that measure reflected energy within several specific sections (also called bands) of the electromagnetic spectrum. Multispectral sensors usually have between 3 and 10 different band measurements in each pixel of the images they produce. It may be obtained using a remote sensing radiometer. Hyperspectral sensors measure energy in narrower and more numerous bands than multispectral sensors. Hyperspectral images can contain as many as 200 (or more) contiguous spectral bands. The numerous narrow bands of hyperspectral sensors provide a continuous spectral measurement across the entire electromagnetic spectrum and therefore are more sensitive to subtle variations in reflected energy. Images produced from hyperspectral sensors contain much more data than images from multispectral sensors. In general, it derives from an imaging spectrometer.

In the context of the present invention, hyperspectral sensors and processing systems are used for detecting and evaluating quality of fruits and vegetables. It is noted that the hyperspectral technique identifies unique 'fingerprints' in the electromagnetic spectrum, also known as spectral signatures. These 'fingerprints' enable identification of, for example, specific parameters, defects, diseases, materials or ingredients of a fruit or vegetable. It is within the scope that the system of the present invention comprises hyperspectral imaging providing spatially resolved information on the nature of chemical species that can be further used to locate damages or defects within or upon the surface of fruits and/or vegetables (e.g. moisture, chemical transformations etc.).

It is further within the scope of the present invention to use hyperspectral remote sensing, for example by wireless network, wireless network interface card (NIC) or Bluetooth.

According to further embodiments of the present invention, the system and method of the present invention combines the usage of hyperspectral imaging and near infrared (NIR) spectrometry or reflectance.

Embodiments of the present invention further provide a connected system for providing lighting, comprising one or more lighting devices, for example, a stereoscopic camera, a hyperspectral camera, a near infrared camera or device.

Embodiments of the present invention can further provide a method of hyperspectral imaging, comprising acquiring, via one or more cameras, one or more image frames of a plurality of fruits or vegetables; transmitting the one or more image frames to a processor; generating, via the processor, one or more analysis results representing at least one of fruit or vegetable parameter or value results; storing the one or more analysis results and image frames in a database and calculating, and presenting to a user, a score for the vegetable or fruit based on matching the image and reflection analyses results with the profile of the fruit or vegetable or with the database.

As used herein, the term "list of attributes" refers to a list of characteristics of the object that a score is being calculated.

In the context of the present invention, non-limiting examples of attributes include BRIX (%), Firmness (sh), Size (mm), Dry Weight (%), Quality Defect, Condition Defect, Color range (e.g. 1-12 Checklist), Stem Color (1-3), Acidity, Hue, Color Variance, Appearance Defect, Color (e.g. 1-50), Color Coverage (%), Starch (%), Size Group, Color Coverage Group, Weight, Juice (%), Seeds (%), Color (e.g. 1-7), Temperature, TSS/Acidity and any other attribute concerning fruit or vegetable properties and any combination thereof.

According to further aspects, the configurable application is capable of scoring vegetable(s) or fruit(s) based on hyperspectral and/or NIR imaging processed by a controller configured to analyze reflectance of hyperspectral and/or NIR imaging devices from the vegetable or fruit, and to image and analyze attributes including characteristics and/or defects of a fruit or vegetable or of a plurality of fruits or vegetables (e.g. fruit or vegetable delivery).

It is within the scope of the present invention that non limiting examples of defects detectable and processed by the system, method and configurable application of present invention include color defect, skin defect, healed wounds, insect damage, cracks, softness, decay, handling damage, dehydration, pests, over mature, disease damage, freezing damage, bruising hail damage or any other extreme weather condition damage, bird damage, bitter pit, bleeding, brown berries, burnt berries, cork, cracks, creasing, foreign bodies, humidity damage, internal breakdown, mold, oleocellosis, split seed, open stones, wounds, pedicle tear, pitting, puffed scald, scars, shatter shelling, soft shoulder, split berries, thin peel, unhealed wounds, watercore, watery, weak, berry drop, black navel, bottleneck, broken berries, Clusters or Triples, defect in shape, deformed, dirty/dusty, green fruits, immature fruits, inking, lenticel, long peduncle, loose low color, mealybug, moth, navel tear, no pedicle, Oidium, open navel, pendulum, pests, poorly brushed, powdery mildew, presence of pedicel, protruding navel, Pruina, rest of flower, Round Rugged Russet, scurfy silver, soft scale, sooty mold, split, stains, sunburn, tight, underweight, undersized, waste, without Rosetta, and any other possible fruit or vegetable defect (for example caused by biotic or abiotic causes or conditions) and any combination thereof.

It is further within the scope of the current invention that in the field of hyperspectral imaging, several image acquisition methods exist, including spectrum scanning techniques, snapshot image acquisition, spatial scanning image acquisition, and spectral-spatial scanning image acquisition. It is acknowledged that hyperspectral imaging devices produce a substantial amount of 'raw' or unprocessed data. In order to make this data relevant in a horticultural or other commercial context, the raw data must be processed to generate an analysis frame, which can then be further analyzed by computer vision algorithms also referred to as a configurable application to generate quantifiable data (analysis results).

In one embodiment provided herein, the camera includes a hyperspectral camera exhibiting several channels, each having a unique spectral response. In an embodiment of the invention, the camera exhibits a response in the range of 400-1000 nm. In other embodiments, the camera can include a hyperspectral camera exhibiting a response in the range of and 900-1700 nm. It is emphasized that the spectral response may include any number of values throughout the range. For example, for a range of 400-900 it may reflect a value for every range point (e.g. value for 400 nm, 401 nm, 402 nm, etc. up to 900 nm). According to other aspects, the spectral response includes only partial values (e.g. X values) within the range (for example, values of 480, 517, 690, 730, 850—only 5 value points).

As used herein, the term "color range" refers hereinafter to a range of color, 1-N, grading the color from the color of un-ripened fruit (example, green for tomatoes) to the color of over-ripened fruits (e.g. dark red for tomatoes).

The term "stone fruit" also called a drupe, is a fruit with a large "stone" inside. The stone is sometimes called the seed, however the seed is inside the stone. The stones can also be called a pit. Examples of stone fruits are peaches, nectarines, plums, lychees, mangoes, almonds, apricots and cherries. These fruits are edible and can be used in cooking.

The term "Open stones" refers hereinafter to a defect in stone fruit where the seed is split, not whole.

The term "Cork" as used herein refers to symptoms on fruits (e.g. apple) or vegetables caused by boron deficiency. There are two major phases of the disease on the fruit: external cork, characterized by surface spots and internal cork, characterized by lesions in the flesh.

The term "watercore" as used herein refers to a symptom of fruits or vegetables characterized by a translucent water-soaked appearance, initially associated with vascular bundles of the coreline or cortex. Watercore symptoms can be expressed as radial or block types. Watercore development, morphology and severity of symptoms can be differ among growing regions and stress conditions.

The term "bitter pit" as used herein refers to a disorder in fruits, especially apples and pears induced by calcium deficiency. The affected fruit have dark spots, about ½ cm diameter, which occur on the skin or in the flesh or both. The cells in the spots are dead (necrotic), and turn brown-black.

The term "bleeding" refers hereinafter to an open cut that juice from a fruit or vegetable drops are getting out from it.

The term "pedicle tear" refers hereinafter to a defect in fruits having pedicle, such as cherries, where the pedicle is torn.

The term "pitting" refers hereinafter to small holes in the peal of fruits, especially citrus fruits, sometimes caused by pests.

The term "soft shoulder" refers hereinafter to a defect in stone fruits, such as peaches, where an area approximate to the peal is soft and brown.

The term "watery" refers hereinafter to a defect type in a fruit or vegetable where excess of water exist in the fruit or vegetable pulp.

The term "weak" refers hereinafter especially to a defect in grapes which are connected weakly to the rachis's cluster.

The term "black navel" refers to a defect or damage in specific orange varieties with a navel, where a black color appears in the navel's area.

The term "bottleneck" refers hereinafter to a deformed shape of round fruits.

The term "clusters or triples" refers hereinafter to two or three cherries connected together via their pedicles. It should be emphasized that this is not a classical defect characteristic of a fruit, but rather a condition that prevents them from being processed in an automatic packing machine.

The term "navel tear" refers hereinafter to a defect in specific orange varieties with a navel, where a tear or scratch appears in the navel area.

The term "open navel" refers hereinafter to a defect in specific orange varieties with a navel, having a hole in the navel area.

The term "pendulum" refers hereinafter to a bruise caused by a machine with a pendulum-like part.

The term "rest of flower" refers hereinafter to a defect of a plant where residues of the flower, that the fruit was created from, stayed connected to the fruit, The term "split" refers hereinafter to a defect in fruits or vegetables that are divided naturally into two parts, for example two fruits combined together.

The term "stains" as used hereinafter refers to dots that appear on the peal of the fruit or vegetable.

The term "tight" refers hereinafter to a defect in grapes, where there are too many or excess of berries in the cluster.

The term "oleocellosis" refers hereinafter to a spotting of fruits, particularly citrus fruits by oil liberated from the oil glands of the rind. It is called also green spot.

As used herein, the terms "scoring" or "score calculations" refer to a set of rules which are applied on a list of attributes and determine the distribution of a score on each one of the attributes in the list.

As used herein, the term "total score" refers to a target number that is associated to an object. The total score is an accumulation of the score of each attribute in the list of attributes. E.g., the range of a total score may be '0' to '100'.

As used herein, the term "scoring group" refers to a classification of a total score of an object in comparison to other objects.

As used herein, the term "list of multiple-level scoring groups" refers to multiple scoring groups which each total score may be associated to. The list of multiple-level groups is arranged in a predefined order. E.g., the scoring groups may be arranged in an ascending order when the range of the total score is between '0' and '100' and four groups are designated as follows: the total score of '100'-'76' is associated to scoring group "A", the total score of '75'-'51' is associated to scoring group "B", the total score of '50'-'26' is associated with scoring group "C" and the total score of '25'-'0' is associated with scoring group "D".

As used herein, the term "weight" refers to the maximum score of an attribute in the list of attributes.

As used herein, the term "configuration type" refers to the contribution of an attribution score to the total score when the value of the attribute is below a predefined minimum value or above a predefined maximum value. E.g., when the configuration type is set to "high" or "middle" and value of the attribution is below a predefined minimum value, the score of the attribute is zeroed. when the configuration type is set to "high" and the value of the attribution is above a predefined maximum value it gains the maximum attribute score. When the configuration type is set to "low" or "middle" and value of the attribution is above a predefined maximum value, the score of the attribute is zeroed.

As used herein, the term "termination flag" refers to a condition when one of the attributes in the list of attributes does not meet the requirement of the predefined minimum value or predefined maximum value or both and as a result the total score is zeroed.

As used herein, the term "Brix" refers to the sugar content of an aqueous solution. According to further aspects, Brix is a unit of measurement to assess any dissolved solids in plant (fruit and vegetable) juices. These solids include amino acids, proteins, minerals, vitamins, and the sugars fructose and sucrose.

As used herein, the term "color, range" refers hereinafter to a range of color, 1-N, grading the color from the color of un-ripened fruit (example, green for tomatoes) to the color of over-ripened fruits (e.g. dark red for tomatoes).

In some embodiments of the present disclosure, a configurable application for scoring an object is provided herein. The configurable application may comprise a configuration interface which is illustrated in FIG. 1 and a processing unit which is illustrated in FIG. 2.

Figure 2:
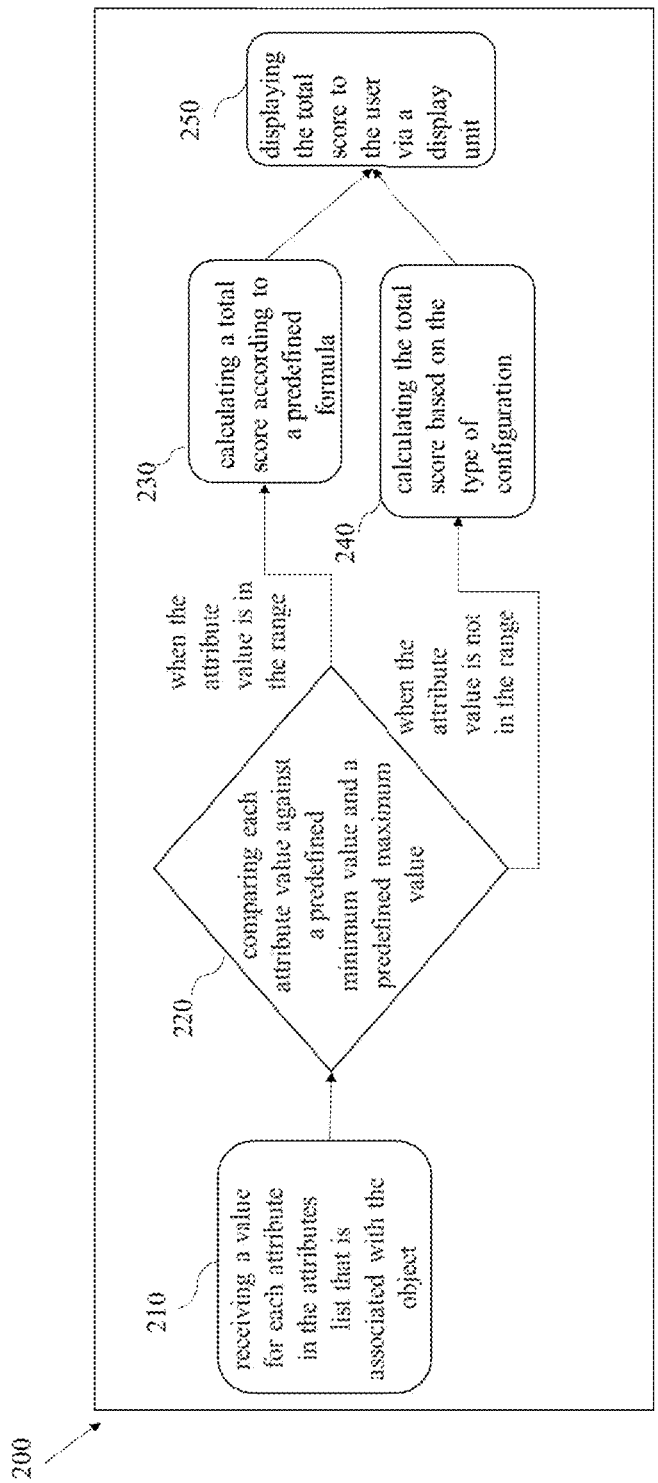
FIG. 2 is a is a high-level flow diagram depicting a processing unit 200 to perform scoring for an object, according to the configuration parameters, in accordance with some embodiments of the present disclosure.

FIG. 1 is a high-level flow diagram depicting a configuration interface 100 to configure an application, in accordance with some embodiments of the present disclosure. This figure shows a configuration interface for configuring an application.

According to some embodiments, in operation 110 the configuration method may comprise:
receiving configuration parameters for each object from a user. The configuration parameters may include: (a) a list of attributes to be associated with an object; (b) a maximum total score; (c) for each attribute in the list of attributes: (i) a minimum value; (ii) a maximum value; and
(iii) weight and (d) a type of configuration.

In a non-limiting example, the object may be a fruit or vegetable. The user may configure the configurable application for scoring an object via the configuration interface 100 with the following configuration parameters 110. The list of attributes to be size and Brix as depicted in the table in FIG. 3. The weight of each attribute in the list of attributes i.e., the maximum total score to be '100', the weight of Brix to be 60% out of the total score and the weight of size to be 40% out of the total score. The user may further configure the configurable application for scoring an object via the configuration interface 100 with minimum and maximum values for each attribute minimum value for Brix to be '0' 6', the maximum value for Brix to be '15' and the minimum value for size to be '10' and the maximum value for size to be '20'. The user may configure the type of configuration to be "high".

According to some embodiments, the configurable application for scoring an object may calculate a total score for an object based on received values of the attributes in the list of attributes.

Figure 3:
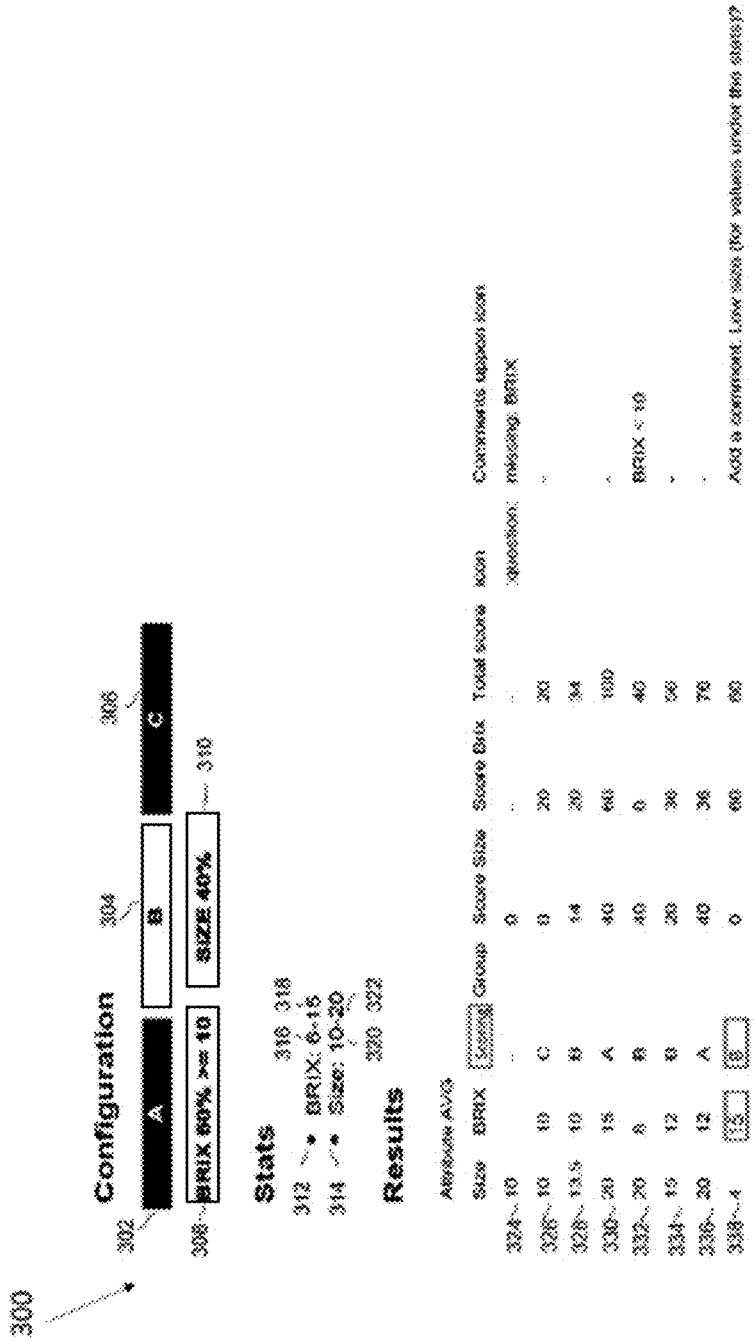
FIG. 3 is a screenshot depicting the scoring of objects which have been calculated based on configuration parameters, in accordance with some embodiments of the present disclosure.

According to some embodiments, the configurable application for scoring may receive from the user a list of multiple-level scoring groups and associate the total score with a group in the list of multiple-level scoring groups and display it to the user via a display unit as depicted in detail in FIG. 3.

FIG. 2 is a high-level flow diagram depicting a processing unit 200 to calculate scoring for an object, according to the configuration parameters, in accordance with some embodiments of the present disclosure. This figure shows a processing unit to calculate scoring for an object.

According to some embodiments, the processing unit 200 to calculate scoring for an object may comprise operation 210 which includes receiving a value for each attribute in the attributes list that is associated with the object. The value for each attribute may be based on image analysis results and on reflection analysis results of the object. In some embodiments, the object may be a fruit or vegetable.

According to some embodiments, the processing unit 200 to calculate scoring for an object may comprise operation 220 which includes comparing each attribute value against a predefined minimum value and a predefined maximum value.

According to some embodiments, when the attribute value is in the range of the predefined minimum value and the predefined maximum value, the processing unit 200 to calculate scoring for an object may comprise operation 230 which includes calculating a total score according to a predefined formula.

According to some embodiments, the predefined formula may be (the attribute value–the predefined minimum value)/(the predefined maximum value–the predefined minimum value)*the weight.

According to some embodiments, when the attribute value is not in the range of the predefined minimum value and the predefined maximum value, the processing unit 200 to calculate scoring for an object may comprise operation 240 which includes calculating the total score based on the type of configuration. In some embodiments, the type of configuration may be selected by the user between "high", "middle" and "low".

According to some embodiments, the processing unit 200 to calculate scoring for an object may comprise operation 250 which includes displaying the total score to the user via a display unit as further depicted in detail in FIG. 3.

FIG. 3 is a screenshot depicting the scoring of objects 300 which have been calculated based on configuration parameters depicted in FIG. 1 and the score calculating depicted in FIG. 2, in accordance with some embodiments of the present disclosure.

According to some embodiments, when the value of the attribute is between a range of minimum and maximum which is retrieved from a database of statistics values of the object, the score of the attribute may be calculated according to a predefined formula. In a non-limiting example, the formula may be (the attribute value–the predefined minimum value)/(the predefined maximum value–the predefined minimum value)*the weight.

According to some embodiments, the user may set a minimum value and/or a maximum value to each attribute of the object, and when the value of the attribute is higher than the predefined minimum which has been retrieved from the database of statistics value the calculation of the score of the attribute may be based on association to predefined groups.

According to some embodiments, in a non-limiting example, the object is a fruit, or a vegetable and the configuration parameters may be as follows: the number of multiple-level scoring groups is configured to be '0' 3', and the scoring groups are 'A' 302, 'B' 304 and 'C' 306. Meaning, the calculated total score which is in the range of '100'-'67' will be associated with scoring group 'A', the calculated total score which is in the range of '66'-'33' will be associated with scoring group 'B', the calculated total score which is in the range of '32'-'0' will be associated with scoring group 'C'. The list of attributes of the object includes: Brix 308 and size 310. The weight of Brix 308 has been configured to be 60% and the weight of size has been configured to be 40%. The user has configured the value of Brix 308 to be equal or more than '10'.

According to some embodiments, in a non-limiting example, the configuration parameters further include: the range of the predefined minimum value and the predefined maximum value which has been configured based on big data statistics where Brix 312 is '0' 6-15', and the predefined minimum 316 is '6' and the predefined maximum 318 is '15'. Based on big data statistics the range of the predefined minimum value and the predefined maximum value of size 314 is '10-20', the predefined minimum 320 is '10' and the predefined maximum value 322 is '20'.

According to some embodiments, each row in the results table 340 represents a fruit or a vegetable. In a non-limiting example, in row 324 the received value of the size of the fruit or the vegetable is '10'. No value was received for Brix.

Therefore, the configurable application for scoring an object may not score the fruit or vegetable and may not associate it to a scoring group. In the comments area in the results table 340 there may be the following comment "missing BRIX".

According to some embodiments, in a non-limiting example, in row 326 the received value of the size is '10' and the received value of Brix is '10'. Since the value of size is in the predefined range of predefined minimum and maximum values, the configurable application for scoring an object may use the predefined formula which may be (the attribute value–the predefined minimum value)/(the predefined maximum value–the predefined minimum value) *the weight, to calculate the score of size. Hence, the calculation for size may be: (10-10)/(20-10)*40 which results in '0' 0'. The value of Brix is '10' which is equal to the value that the user configured and thus the calculation for Brix may be based on association to predefined groups which results in '20'. The total score is '20' and the scoring group of the fruit or vegetable is 'C'.

According to some embodiments, in a non-limiting example, in row 328 the received value of the size is '13.5' and the received value of Brix is '10'. Since the value of size is in the predefined range of predefined minimum and maximum values, the configurable application for scoring an object may use the predefined formula which may be (the attribute value–the predefined minimum value)/(the predefined maximum value–the predefined minimum value) *the weight, to calculate the score of size. Hence, the calculation for size may be: (13.5-10)/(20-10)*40 which results in '14'. The value of Brix is '10' which is equal to the value that the user configured and thus the calculation for Brix may be based on association to predefined groups which results in '20'. The total score is '34' and the scoring group of the fruit or vegetable is 'B'.

According to some embodiments, in a non-limiting example, in row 330 the received value of the size is '20' and the received value of Brix is '15'. Since the value of size is in the predefined range of predefined minimum and maximum values, the configurable application for scoring an object may use the predefined formula which may be (the attribute value–the predefined minimum value)/(the predefined maximum value–the predefined minimum value) *the weight, to calculate the score of size. Hence, the calculation for size may be: (20-10)/(20-10)*40 which results in '40'. The value of Brix is '15' which is higher than the value that the user configured and thus the calculation for Brix may be based on association to predefined groups which results in '60'. The total score of all attributes is accumulated to a total score of '100' which is associated to scoring group 'A'.

According to some embodiments, in a non-limiting example, in row 332 the received value of the size is '20' and the received value of Brix is '0' 8'. Since only the value of size is in the predefined range of predefined minimum and maximum values, the configurable application for scoring an object may use the predefined formula which may be (the attribute value–the predefined minimum value)/(the predefined maximum value–the predefined minimum value) *the weight, to calculate the score of size. Hence, the calculation for size may be: (20-10)/(20-10)*40 which results in '40'. Since the value of Brix is less than the minimum value that has been configured by the user, i.e., '10' then the score of Brix is zeroed. In the comment area the following text may be presented: "BRIX<10"

According to some embodiments, in a non-limiting example, in row 334 the received value of the size is '15' and the received value of Brix is '12'. Since the value of size is in the predefined range of predefined minimum and maximum values, the configurable application for scoring an object may use the predefined formula which may be (the attribute value–the predefined minimum value)/(the predefined maximum value–the predefined minimum value) *the weight, to calculate the score of size. Hence, the calculation for size may be: (15-10)/(20-10)*40 which results in '20'. The value of Brix is '12' which is higher than the value that the user configured and thus the calculation for Brix may be based on association to predefined groups which results in '36'. The total score of all attributes is accumulated to a total score of '56' which is associated to scoring group 'B'.

According to some embodiments, in a non-limiting example, in row 336 the received value of the size is '20' and the received value of Brix is '12'. Since the value of size is in the predefined range of predefined minimum and maximum values, the configurable application for scoring an object may use the predefined formula which may be (the attribute value–the predefined minimum value)/(the predefined maximum value–the predefined minimum value) *the weight, to calculate the score of size. Hence, the calculation for size may be: (20-10)/(20-10)*40 which results in '40'. The value of Brix is '12' which is higher than the value that the user configured and thus the calculation for Brix may be based on association to predefined groups which results in '36'. The total score of all attributes is accumulated to a total score of '76' which is associated to scoring group 'A'.

According to some embodiments, in a non-limiting example, in row 338 the received value of the size is '4' and the received value of Brix is '15'. Since the value of size is '4' which is less than the minimum value (big data statistics) then its score is zeroed. The value of Brix is '15' which is higher than the value that the user configured and thus the calculation for Brix may be based on association to predefined groups which results in '60'. The total score of all attributes is accumulated to a total score of '100' which is associated to scoring group 'B'.

According to some embodiments, each attribute in the list of attributes has a termination flag associated to it, and the user may configure it as 'turned off' or 'turned on'. When the termination flag of an attribute is turned on, the processing unit, e.g., processing unit 200 (FIG. 2) of the configurable application for scoring an object, may be further arranged to zero the total score based on the configuration type and hence, associating the total score of the object to the lowest scoring group.

According to some embodiments, when the configuration type is "high" the processing unit is further arranged to check if the attribute value is less than the predefined minimum; when the configuration type is "middle" the processing unit is further arranged to check if the attribute value is less than the predefined minimum and more than the predefined maximum; and when the configuration type is "low" the processing unit is further arranged to check if the attribute value is more than the predefined maximum.

According to some embodiments, the configurable application is cloud based.

According to some embodiments, the received value for each attribute in the attributes list is based on image analysis results and on reflection analysis results of the object.

Figure 4A:
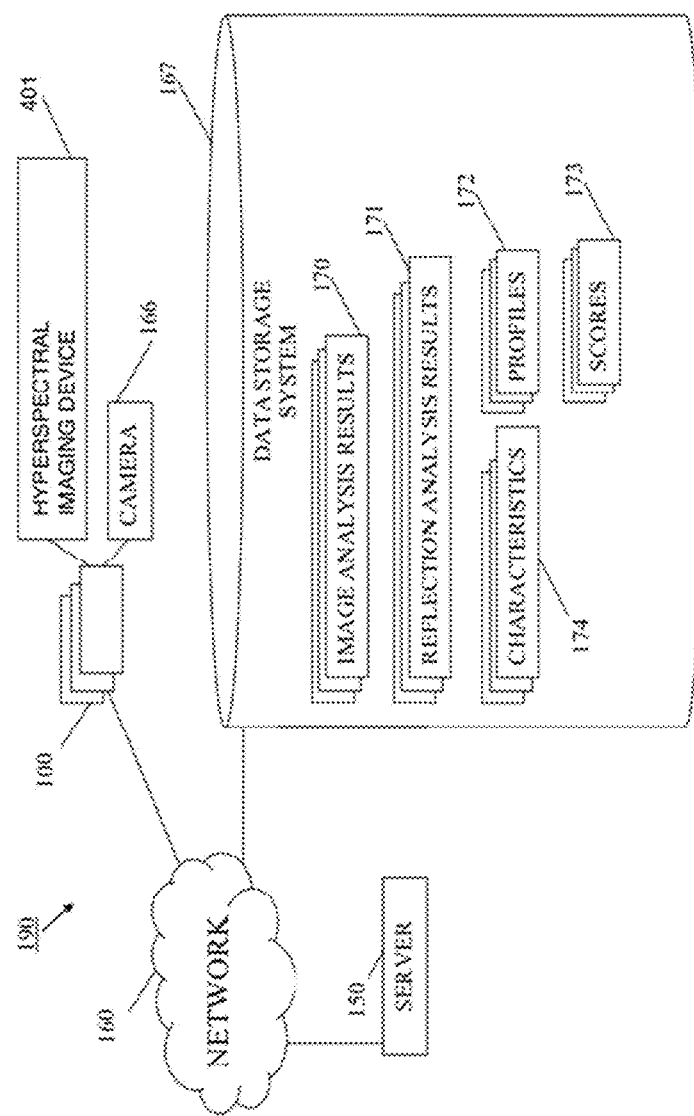
FIG. 4A shows high level block diagram of a system comprising hyperspectral imaging device according to illustrative embodiments of the present invention.

Reference is made to FIG. 4A, showing a high-level block diagram of a system 190 according to some alternative embodiments of the present invention. As shown, a system may include a plurality of computing systems or devices 100

(e.g., a plurality of users' smartphones or other mobile communication devices), a server 150 and a digital data storage system 167 that may be, or may be similar to, storage systems 130 and/or 151. As shown, some of computing devices 100 may include, or may be connected to, a camera 166 and hyperspectral imaging device 401. Camera 166 may be any suitable image acquisition device capable of obtaining an image of an object, for example, in some embodiments, camera 166 is included in a smartphone as known in the art. In one embodiment, at least one camera 166 with communication capability can be arranged. In this embodiment, the camera 166 can acquire an image frame of the vegetable(s) or fruit(s) and can transmit the image frame to a processor which can generate an analysis result 170 based on an image processing algorithm also referred to as a configurable application and stores the result 170 in a database. In various embodiments, image processing algorithms also referred to as a configurable applications are utilized to process at least one image having at least one spectral response channel, producing analysis results 170 representing characteristics 174, profile 172 and scores 173.

Hyperspectral imaging 401 may be a device that emits light onto an object (e.g., a fruit or vegetable) and receives or senses (e.g., using a built-in sensor) light reflected from the object.

According to further embodiments of the present invention, device 401 may be a hyperspectral imaging device, as an optical tool for contiguous high-resolution spectrometry used for identification and characterization of materials, characteristic parameters and defects of a fruit or a vegetable.

As shown, data storage system 167 may store or include image analysis results 170, reflection analysis results 171, profiles 172, scores 173 and characteristics 174. Profiles 172 may be, or may include, any information in profile 220 as described herein and scores 173 may be, or may include, any information in scores 221 as described herein. Image analysis results 170, reflection analysis results 171, profiles 172, scores 173 and characteristics 174 may be, or may include, any suitable digital data structure or construct or computer data objects that enable storing, retrieving and modifying digital data, values or information. For example, some of image analysis results 170, reflection analysis results 171, profiles 172, scores 173 and characteristics 174 may be or may include files, tables or lists in a database in storage system 167. For example, some of image analysis results 170, reflection analysis results 171, profiles 172, scores 173 and characteristics 174 may each include several fields that can be digitally set or cleared by controller 105, a plurality of parameters for which values can be set by controller 105, a plurality of entries that may be modified by controller 105 or by server 150 and so on. For the sake of simplicity, image analysis results 170, reflection analysis results 171, profiles 172, scores 173 and characteristics 174 may be collectively referred to herein, e.g., by image analysis results 170 or individually, e.g., by image analysis result 170.

Figure 4B:
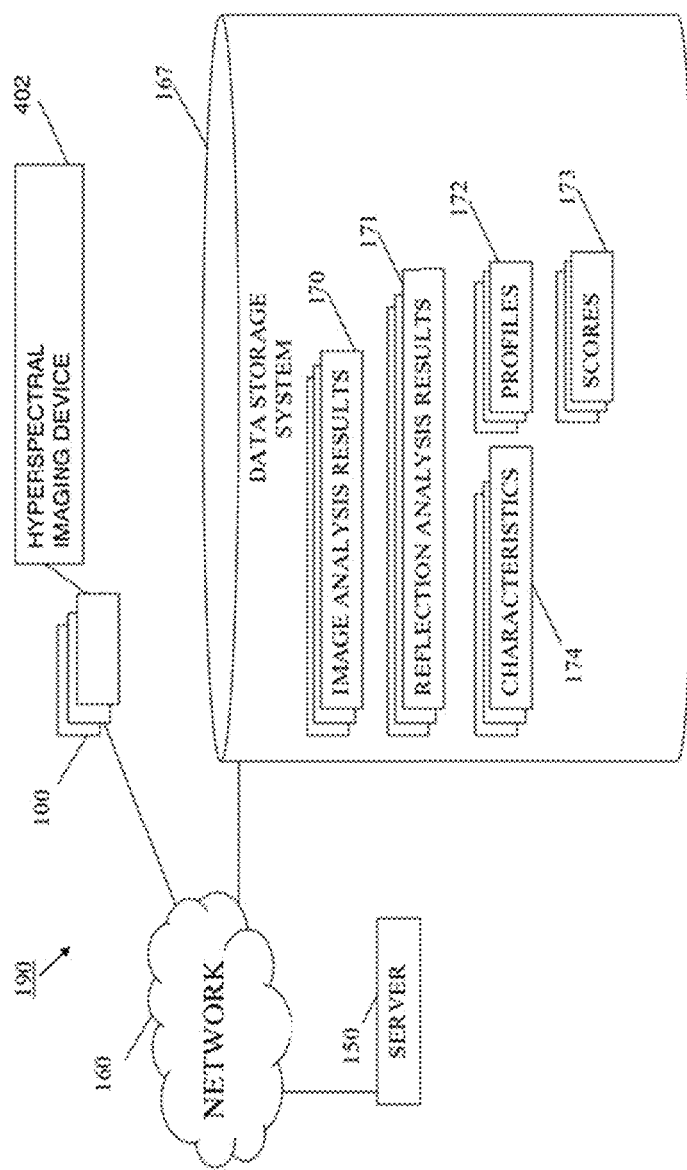
FIG. 4B shows high level block diagram of a system comprising hyperspectral imaging device according to alternative illustrative embodiments of the present invention.

Reference is made to FIG. 4B, showing a high-level block diagram of a system 190 according to some alternative embodiments of the present invention. As shown, a system may include a plurality of computing systems or devices 100 (e.g., a plurality of users' smartphones or other mobile communication devices), a server 150 and a digital data storage system 167 that may be, or may be similar to, storage systems 130 and/or 151. As shown, some of computing devices 100 may include, or may be connected to, a hyperspectral imaging device 402. In this embodiment, the hyperspectral imaging device 402 is a hyperspectral camera capable of obtaining an image of an object, for example, in some embodiments, included in a smartphone as known in the art. Hyperspectral imaging 402 may be a device that emits light onto an object (e.g., a fruit or vegetable) and receives or senses (e.g., using a built-in sensor) light reflected from the object.

According to other embodiments of the present invention, device 402 may be a hyperspectral imaging device, as an optical tool for contiguous high-resolution spectrometry used for identification and characterization of materials, characteristic parameters and defects of a fruit or a vegetable.

According to further embodiments, the present invention discloses the configurable application as defined in any of the above, wherein the processing unit uses a machine learning algorithm.

According to further embodiments, the present invention discloses the configurable application as defined in any of the above, wherein the machine learning algorithm uses verified training data.

According to further embodiments, the present invention discloses a method of non-destructively determining characteristics of a vegetable or fruit, the method comprising:
creating at least one profile for a cultivar of a vegetable or fruit;
processing an image of a vegetable or fruit to produce image analysis results;
analyzing hyperspectral and/or Near Infrared (NIR) illumination reflected from the vegetable or fruit to produce reflection analysis results; and
calculating, and presenting to a user, a score for the vegetable or fruit based on matching the image and reflection analyses results with the profile.

According to further embodiments, the present invention discloses the method as defined in any of the above, wherein said calculating is performed using the configurable application as defined in any of the above.

According to further embodiments, the present invention discloses the method as defined in any of the above, wherein the profile and the analysis results include a value that represents a ripeness and a value that represents a quality.

According to further embodiments, the present invention discloses the method as defined in any of the above, further comprises steps of analyzing a value using a device selected from the group consisting of: a refractometer, a pH meter, acidometer, penetrometer, durometer, temperature meter and any combination thereof.

According to further embodiments, the present invention discloses the method as defined in any of the above, wherein said analyzing step comprises analyzing a value selected from the group consisting of: BRIX %, firmness, size, dry weight %, quality defect, condition defect, color range, stem color, acidity, hue, color variance, appearance, color coverage, starch (%), size group (%), color coverage group, weight, juice (%), seeds (%), temperature, TSS/acidity and any combination thereof.

According to further embodiments, the present invention discloses the method as defined in any of the above, wherein said analyzing step comprises analyzing a defect type selected from the group consisting of color defect, skin defect, healed wounds, insect damage, cracks, softness, decay, handling damage, dehydration, pests, over mature, disease damage, freezing damage, bruising hail damage or any other extreme weather condition damage, bird damage, bitter pit, bleeding, brown berries, burnt berries, cork, cracks, creasing, foreign bodies, humidity damage, internal breakdown, mold, oleocellosis, split seed, open stones, wounds, pedicle tear, pitting, puffed scald, scars, shatter shelling, soft shoulder, split berries, thin peel, unhealed wounds, watercore, watery, weak, berry drop, black navel, bottleneck, broken berries, Clusters or Triples, defect in shape, deformed, dirty/dusty, green fruits, immature fruits, inking, lenticel, long peduncle, loose low color, mealybug, moth, navel tear, no pedicle, Oidium, open navel, pendulum, pests, poorly brushed, powdery mildew, presence of pedicel, protruding navel, Pruina, rest of flower, Round Rugged Russet, scurfy silver, soft scale, sooty mold, split, stains, sunburn, tight, underweight, undersized, waste, without Rosetta, and any other possible fruit or vegetable defect (for example caused by biotic or abiotic causes or conditions) and any combination thereof.

According to further embodiments, the present invention discloses the method as defined in any of the above, further comprising:
  obtaining a cultivar of the vegetable or fruit; and
  calculating the at least one value based on the cultivar.

According to further embodiments, the present invention discloses the method as defined in any of the above, further comprising calculating the score based on at least one of: a geographic region and a date.

According to further embodiments, the present invention discloses the method as defined in any of the above, further comprising:
  receiving an image of a plurality of vegetables or fruits; and
  calculating, for the plurality of vegetables or fruit, scores of the best and worst vegetable or fruit.

According to further embodiments, the present invention discloses the method as defined in any of the above, further comprising calculating a prediction related to at least one of: harvesting and treating of crops.

According to further embodiments, the present invention discloses the method as defined in any of the above, further comprising:
  receiving, from a plurality of users, profiles and associated scores; and
  creating the profile and associating the profile with a score based on the profiles and associated scores received from the users.

According to further embodiments, the present invention discloses the method as defined in any of the above, further comprising using input from a plurality of users for at least one of: creating the profile and calculating the score.

According to further embodiments, the present invention discloses the method as defined in any of the above, further comprising:
  designating at least one of: a profile and a score, as a reference; and
  calculating the at least one value based on comparing at least one reference to at least one of: the image analysis results and the reflection analysis results.

According to further embodiments, the present invention discloses the method as defined in any of the above, further comprising: causing a machine to select a fruit or vegetable based on at least one of: a profile and a score.

According to further embodiments, the present invention discloses a system comprising:
  a memory; and
  a controller configured to:
    create at least one profile for a cultivar of a vegetable or fruit;
    process an image of the vegetable or fruit to produce image analysis results;
    analyze hyperspectral and/or Near Infrared (NIR) illumination reflected from the vegetable or fruit to produce reflection analysis results; and
    calculate, and present to a user, a score for the vegetable or fruit based on matching the image and reflection analyses results with the profile.

According to further embodiments, the present invention discloses the system as defined in any of the above, wherein said controller is configured to calculate, and present to a user, a score for the vegetable or fruit based on matching the image and reflection analyses results with the profile, using said configurable application as defined in any of the above.

According to further embodiments, the present invention discloses the system as defined in any of the above, wherein the profile and the analyses results include a first value that represents a ripeness and a second value that represents a quality.

According to further embodiments, the present invention discloses the system as defined in any of the above, wherein said controller is configured to analyze a value obtainable using a device selected from the group consisting of: a refractometer, a pH meter, acidometer, penetrometer, durometer, temperature meter and any combination thereof.

According to further embodiments, the present invention discloses the system as defined in any of the above, wherein said controller is configured to analyze a value selected from the group consisting of: BRIX %, firmness, size, dry weight %, quality defect, condition defect, color range, stem color, acidity, hue, color variance, appearance, color coverage, starch (%), size group (%), color coverage group, weight, juice (%), seeds (%), temperature, TSS/acidity and any combination thereof.

According to further embodiments, the present invention discloses the system as defined in any of the above, wherein said controller is configured to analyze a defect type selected from the group consisting of color defect, skin defect, healed wounds, insect damage, cracks, softness, decay, handling damage, dehydration, pests, over mature, disease damage, freezing damage, bruising hail damage or any other extreme weather condition damage, bird damage, bitter pit, bleeding, brown berries, burnt berries, cork, cracks, creasing, foreign bodies, humidity damage, internal breakdown, mold, olcocellosis, split seed, open stones, wounds, pedicle tear, pitting, puffed scald, scars, shatter shelling, soft shoulder, split berries, thin peel, unhealed wounds, watercore, watery, weak, berry drop, black navel, bottleneck, broken berries, Clusters or Triples, defect in shape, deformed, dirty/dusty, green fruits, immature fruits, inking, lenticel, long peduncle, loose low color, mealybug, moth, navel tear, no pedicle, Oidium, open navel, pendulum, pests, poorly brushed, powdery mildew, presence of pedicel, protruding navel, Pruina, rest of flower, Round Rugged Russet, scurfy silver, soft scale, sooty mold, split, stains, sunburn, tight, underweight, undersized, waste, without Rosetta, and any other fruit or vegetable defect and any combination thereof.

According to further embodiments, the present invention discloses the system as defined in any of the above, wherein the controller is further configured to at least one of:
  e. calculate the at least one value based on at least one of: a geographic region and a date.
  f. receive an image of a plurality of vegetables or fruit; and
  calculate, for the plurality of vegetables or fruit, scores of the best and worst vegetables or fruits;
  g. calculate a prediction related to at least one of: harvesting and treating of crops; and h. receive, from a plurality of users, profiles and associated scores; and create the profile and associate the profile with a score based on the profiles and associated scores received from the users.

According to further embodiments, the present invention discloses the system as defined in any of the above wherein the controller is further configured to a. use input from a plurality of users for at least one of: creating the profile and calculating the score;

b. designate at least one of: a profile and a score, as a reference; and calculate the at least one value based on comparing at least one reference to at least one of: the image analysis results and the reflection analysis results; and c. cause a machine to select a fruit or vegetable based on at least one of: a profile and a score.

According to further embodiments, the present invention discloses a method of non-destructively determining characteristics of a vegetable or fruit, the method comprising:

(a) receiving a training set of hyperspectral data using a system comprising;

(i) a memory; and (ii) a controller configured to:

create at least one profile for a cultivar of a vegetable or fruit;

process an image of the vegetable or fruit to produce image analysis results;

analyze hyperspectral illumination reflected from the vegetable or fruit to produce reflection analysis results; and calculate, and present to a user, a score for the vegetable or fruit based on matching the image and reflection analyses results with the profile;

(b) applying a machine learning algorithm to said training set of hyperspectral data to provide predictor parameters for said vegetable or fruit profile;

(c) receiving measurement hyperspectral data from a vegetable or fruit of interest; and using said predictor parameters to score said vegetable or fruit of interest.

wherein said training set of hyperspectral data, and said measurement hyperspectral data comprise reflection spectra across wavelength bands of light that include at least visible, near infrared and short-wave infrared regions of the electromagnetic spectrum.

The invention claimed is:

1. A method of non-destructively determining characteristics of a vegetable or fruit, the method comprising:

creating at least one profile for a cultivar of a vegetable or fruit, processing an image of a vegetable or fruit to produce image analysis results;

analyzing hyperspectral and/or Near Infrared (NIR) illumination reflected from the vegetable or fruit and detected by a hyperspectral imaging device, to produce reflection analysis results; and calculating, and presenting to a user, a score for the vegetable or fruit based on matching the image and reflection analyses results with the profile using a computing system for calculating a total score of a vegetable or a fruit based on parameters of the vegetable or fruit configured by a user, the computing system comprising:

a configurable application comprising a configuration interface, said configuration interface is arranged to:

receive configuration parameters predefined by the user for the vegetable or fruit, wherein the configuration parameters include:

a. a list of attributes to be associated with a vegetable or a fruit;

b. a maximal total score for the vegetable or fruit;

c. for each attribute in the list of attributes: (i) a minimum value, (ii) a maximum value, the minimum value and the maximum value are retrieved from a database of statistics values of the vegetable or fruit, and (iii) weight calculated as a predefined maximum score for an attribute out of the maximal total score of the vegetable or fruit, and d. a type of configuration for each attribute, the type of configuration is selected from (i) "high"; (ii) "low"; or (iii) "middle";

a processing unit, said processing unit is arranged to calculate the total score for the vegetable or fruit according to the received configuration parameters, by:

a. receiving a value for each attribute in the attributes list that is associated with the vegetable or fruit;

b. comparing each attribute value against a predefined minimum value and a predefined maximum value of the attribute;

c. calculating an attribute score according to a predefined formula, when the attribute value is in the range of the predefined minimum value and the predefined maximum value;

d. calculating an attribute score based on the type of configuration, when the attribute value is not in the range of the predefined minimum value and the predefined maximum value; wherein when the type of configuration is "high":

i. when the attribute value is less than the predefined minimum value, scoring the attribute score as zero; and ii. when the attribute value is more than the predefined maximum value, scoring the attribute as the predefined maximum attribute score;

when the type of configuration is "middle":

iii. when the attribute value is less than the predefined minimum value, scoring the attribute score as zero; and iv. when the attribute value is more than the predefined maximum value, scoring the attribute score as zero; and when the type of configuration is "low":

v. when the attribute value is less than the predefined minimum value, scoring the attribute as the predefined maximum attribute score; and vi. when the attribute value is more than the predefined maximum value, scoring the attribute score as zero;

e. calculating the total score of the vegetable or fruit as an accumulation of the score of each attribute in the list of attributes; and f. displaying the total score of the vegetable or fruit to a user via a display unit, wherein the calculating is performed only when all attributes have values.

2. The method of claim 1, wherein at least one of the following holds true:

a. the profile and the analysis results include a value that represents a ripeness and a value that represents a quality; and b. the method further comprises steps of analyzing a value using a device selected from the group consisting of: a refractometer, a pH meter, acidometer, penetrometer, durometer, temperature meter and any combination thereof.

3. The method according to claim 1, wherein said analyzing step comprises at least one of:
   a. analyzing a value selected from the group consisting of: BRIX %, firmness, size, dry weight %, quality defect, condition defect, color range, stem color, acidity, hue, color variance, appearance, color coverage, starch (%), size group (%), color coverage group, weight, juice (%), seeds (%), temperature, TSS/acidity and any combination thereof; and
   b. analyzing a defect type selected from the group consisting of color defect, skin defect, healed wounds, insect damage, cracks, softness, decay, handling damage, dehydration, pests, over mature, disease damage, freezing damage, bruising hail damage or any other extreme weather condition damage, bird damage, bitter pit, bleeding, brown berries, burnt berries, cork, cracks, creasing, foreign bodies, humidity damage, internal breakdown, mold, oleocellosis, split seed, open stones, wounds, pedicle tear, pitting, puffed scald, scars, shatter shelling, soft shoulder, split berries, thin peel, unhealed wounds, watercore, watery, weak, berry drop, black navel, bottleneck, broken berries, Clusters or Triples, defect in shape, deformed, dirty/dusty, green fruits, immature fruits, inking, lenticel, long peduncle, loose low color, mealybug, moth, navel tear, no pedicle, Oidium, open navel, pendulum, pests, poorly brushed, powdery mildew, presence of pedicel, protruding navel, Pruina, rest of flower, Round Rugged Russet, scurfy silver, soft scale, sooty mold, split, stains, sunburn, tight, underweight, undersized, waste, without Rosetta, and any other fruit or vegetable defect and any combination thereof.

4. The method of claim 1, further comprising at least one step of:
   obtaining a cultivar of the vegetable or fruit; and calculating the at least one value based on the cultivar;
   calculating the score based on at least one of: a geographic region and a date;
   receiving an image of a plurality of vegetables or fruits; and calculating, for the plurality of vegetables or fruit, scores of the best and worst vegetable or fruit;
   calculating a prediction related to at least one of: harvesting and treating of crops; and
   receiving, from a plurality of users, profiles and associated scores; and creating the profile and associating the profile with a score based on the profiles and associated scores received from the users.

5. The method of claim 4, further comprising at least one step of:
   a. using input from a plurality of users for at least one of: creating the profile and calculating the score;
   b. designating at least one of: a profile and a score, as a reference; and calculating the at least one value based on comparing at least one reference to at least one of: the image analysis results and the reflection analysis results; and
   c. causing a machine to select a fruit or vegetable based on at least one of: a profile and a score.

6. A system comprising:
   a memory;
   a hyperspectral imaging device; and
   a controller configured to:
      create at least one profile for a cultivar of a vegetable or fruit;
      process an image of the vegetable or fruit to produce image analysis results;
      analyze hyperspectral and/or—Near Infrared (NIR) illumination reflected from the vegetable or fruit and detected by the hyperspectral imaging device, to produce reflection analysis results; and
   calculate, and present to a user, a score for the vegetable or fruit based on matching the image and reflection analyses results with the profile using a computing system for calculating a total score of a vegetable or a fruit based on parameters of the vegetable or fruit configured by a user, the computing system comprising:
      a configurable application comprising a configuration interface, said configuration interface is arranged to:
      receive configuration parameters predefined by the user for the vegetable or fruit, wherein the configuration parameters include:
         e. a list of attributes to be associated with a vegetable or a fruit;
         f. a maximal total score for the vegetable or fruit;
         g. for each attribute in the list of attributes: (i) a minimum value, (ii) a maximum value, the minimum value and the maximum value are retrieved from a database of statistics values of the vegetable or fruit, and (iii) weight calculated as a predefined maximum score for an attribute out of the maximal total score of the vegetable or fruit, and
         h. a type of configuration for each attribute, the type of configuration is selected from (i) "high"; (ii) "low"; or (iii) "middle";
      a processing unit, said processing unit is arranged to calculate the total score for the vegetable or fruit according to the received configuration parameters, by:
         g. receiving a value for each attribute in the attributes list that is associated with the vegetable or fruit;
         h. comparing each attribute value against a predefined minimum value and a predefined maximum value of the attribute;
         i. calculating an attribute score according to a predefined formula, when the attribute value is in the range of the predefined minimum value and the predefined maximum value;
         j. calculating an attribute score based on the type of configuration, when the attribute value is not in the range of the predefined minimum value and the predefined maximum value; wherein
            when the type of configuration is "high":
               i. when the attribute value is less than the predefined minimum value, scoring the attribute score as zero; and
               ii. when the attribute value is more than the predefined maximum value, scoring the attribute as the predefined maximum attribute score;
            when the type of configuration is "middle":
               iii. when the attribute value is less than the predefined minimum value, scoring the attribute score as zero; and
               iv. when the attribute value is more than the predefined maximum value, scoring the attribute score as zero; and
            when the type of configuration is "low":
               v. when the attribute value is less than the predefined minimum value, scoring the attribute as the predefined maximum attribute score; and
               vi. when the attribute value is more than the predefined maximum value, scoring the attribute score as zero;

k. calculating the total score of the vegetable or fruit as an accumulation of the score of each attribute in the list of attributes; and l. displaying the total score of the vegetable or fruit to a user via a display unit, wherein the calculating is performed only when all attributes have values.

7. The system of claim 6, wherein the profile and the analyses results include a first value that represents a ripeness and a second value that represents a quality.

8. The system according to claim 6, wherein said controller is configured to at least one of:

a. analyze a value obtainable using a device selected from the group consisting of: a refractometer, a pH meter, acidometer, penetrometer, durometer, temperature meter and any combination thereof;

b. analyze a value selected from the group consisting of: BRIX %, firmness, size, dry weight %, quality defect, condition defect, color range, stem color, acidity, hue, color variance, appearance, color coverage, starch (%), size group (%), color coverage group, weight, juice (%), seeds (%), temperature, TSS/acidity and any combination thereof;

c. analyze a defect type selected from the group consisting of color defect, skin defect, healed wounds, insect damage, cracks, softness, decay, handling damage, dehydration, pests, over mature, disease damage, freezing damage, bruising hail damage or any other extreme weather condition damage, bird damage, bitter pit, bleeding, brown berries, burnt berries, cork, cracks, creasing, foreign bodies, humidity damage, internal breakdown, mold, oleocellosis, split seed, open stones, wounds, pedicle tear, pitting, puffed scald, scars, shatter shelling, soft shoulder, split berries, thin peel, unhealed wounds, watercore, watery, weak, berry drop, black navel, bottleneck, broken berries, Clusters or Triples, defect in shape, deformed, dirty/dusty, green fruits, immature fruits, inking, lenticel, long peduncle, loose low color, mealybug, moth, navel tear, no pedicle, Oidium, open navel, pendulum, pests, poorly brushed, powdery mildew, presence of pedicel, protruding navel, Pruina, rest of flower, Round Rugged Russet, scurfy silver, soft scale, sooty mold, split, stains, sunburn, tight, underweight, undersized, waste, without Rosetta, and any other fruit or vegetable defect and any combination thereof;

d. calculate the at least one value based on at least one of: a geographic region and a date;

e. receive an image of a plurality of vegetables or fruit; and calculate, for the plurality of vegetables or fruit, scores of the best and worst vegetables or fruits;

f. calculate a prediction related to at least one of: harvesting and treating of crops; and g. receive, from a plurality of users, profiles and associated scores; and create the profile and associate the profile with a score based on the profiles and associated scores received from the users.

9. The system of claim 8 wherein the controller is further configured to a. use input from a plurality of users for at least one of: creating the profile and calculating the score;

b. designate at least one of: a profile and a score, as a reference; and calculate the at least one value based on comparing at least one reference to at least one of: the image analysis results and the reflection analysis results; and c. cause a machine to select a fruit or vegetable based on at least one of: a profile and a score.

* * * * *